(12) United States Patent
Pengfei

(10) Patent No.: US 9,782,296 B2
(45) Date of Patent: Oct. 10, 2017

(54) GOGGLE WITH REMOVABLE NOSEGUARD

(71) Applicant: 100% SPEEDLAB, LLC, San Diego, CA (US)

(72) Inventor: Li Pengfei, Chengyang District (CN)

(73) Assignee: 100% SPEEDLAB, LLC, San Diego, CA (US)

( * ) Notice: Subject to any disclaimer, the term of this patent is extended or adjusted under 35 U.S.C. 154(b) by 36 days.

(21) Appl. No.: 14/165,534

(22) Filed: Jan. 27, 2014

(65) Prior Publication Data

US 2014/0208488 A1    Jul. 31, 2014

Related U.S. Application Data

(60) Provisional application No. 61/756,894, filed on Jan. 25, 2013.

(51) Int. Cl.
*A61F 9/00* (2006.01)
*A61F 9/02* (2006.01)
*A63B 33/00* (2006.01)

(52) U.S. Cl.
CPC ............ *A61F 9/029* (2013.01); *A63B 33/002* (2013.01)

(58) Field of Classification Search
CPC . A63B 33/002; A63B 33/00; A63B 2033/004; A63B 2033/006; A63B 33/004; A61F 9/02; A61F 9/029; A41D 13/1184; A41D 13/11; G02C 3/003; G02C 2200/16; G02C 5/12; G02C 5/126

USPC ........ 2/431, 426, 446, 9, 445; 351/136, 137, 351/138

See application file for complete search history.

(56) References Cited

U.S. PATENT DOCUMENTS

| | | | | |
|---|---|---|---|---|
| 2,519,561 | A * | 8/1950 | Gillman | ................... A61F 9/029 2/13 |
| 4,707,089 | A * | 11/1987 | Danloup et al. | ............... 351/138 |
| 4,848,893 | A * | 7/1989 | Grendol | ........................ 351/138 |
| 5,033,128 | A * | 7/1991 | Torres | .................... A62B 18/00 128/205.22 |
| 5,220,689 | A * | 6/1993 | Miller | ..................... A61F 9/029 2/12 |
| 5,379,464 | A * | 1/1995 | Schleger | ................. A61F 9/029 2/431 |
| 5,697,100 | A * | 12/1997 | Horowitz | ........... A41D 13/1161 2/13 |
| 6,145,133 | A * | 11/2000 | Sato et al. | ........................ 2/428 |
| 7,641,333 | B2 * | 1/2010 | Blanshay et al. | ............... 351/47 |
| 2003/0140403 | A1 * | 7/2003 | Chou | .................... A63B 33/002 2/428 |
| 2004/0111779 | A1 * | 6/2004 | Gagnon et al. | ........................ 2/9 |
| 2013/0014316 | A1 * | 1/2013 | Castro et al. | ..................... 2/424 |

\* cited by examiner

*Primary Examiner* — Khaled Annis
(74) *Attorney, Agent, or Firm* — Haynes and Boone, LLP

(57) ABSTRACT

A goggle having a removable noseguard, comprising a flexible goggle frame having a nose region that extends over the bridge of the user's nose, the goggle frame comprising an engagement region that extends from the front of the goggle frame and having a plurality of locking tabs, and a flexible noseguard comprising a channel to receive the engagement region to position the noseguard on the frame and a plurality of notches sized and positioned to receive the plurality of locking tabs to firmly attach the noseguard to the goggle frame.

12 Claims, 10 Drawing Sheets

US 9,782,296 B2

GOGGLE WITH REMOVABLE NOSEGUARD

This application claims the benefit of U.S. Provisional Patent Application No. 61/756,894 filed on Jan. 25, 2013, and which is hereby incorporated by reference in its entirety as if set forth herein.

BACKGROUND OF THE INVENTION

Field of the Invention

The invention relates generally to the field of protective goggles. In particular, the invention relates to goggles with removable noseguards for use in various sports.

Description of Related Art

Prior art goggles have used removable noseguards that can be attached and detached by the user to protect the nose area from dirt, rocks, and other debris. However, prior art removable noseguards have been difficult to remove and attach by the user. The present invention is a removable noseguard that can be quickly and easily attached and removed from the goggle frame.

SUMMARY OF THE INVENTION

A goggle having a removable noseguard, comprising a flexible goggle frame having a nose region that extends over the bridge of the user's nose, the goggle frame comprising an engagement region that extends from the front of the goggle frame and having a plurality of locking tabs, and a flexible noseguard comprising a channel to receive the engagement region to position the noseguard on the frame and a plurality of notches sized and positioned to receive the plurality of locking tabs to firmly attach the noseguard to the goggle frame. In various exemplary embodiments, the locking tabs have a forward facing surface that is angled from front to back, and a back facing surface that extends generally perpendicular from the generally planar surface of the goggle frame. In various exemplary embodiments, the locking tabs may have a generally triangular cross-section. In various exemplary embodiments, the locking tabs may have a generally quadrilateral cross-section.

DETAILED DESCRIPTION OF THE PREFERRED EMBODIMENTS

The following description is presented to enable any person skilled in the art to make and use the invention. For purposes of explanation, specific nomenclature is set forth to provide a thorough understanding of the present invention. Descriptions of specific embodiments or applications are provided only as examples. Various modifications to the embodiments will be readily apparent to those skilled in the art, and general principles defined herein may be applied to other embodiments and applications without departing from the spirit and scope of the invention. Thus, the present invention is not intended to be limited to the embodiments shown, but is to be accorded the widest possible scope consistent with the principles and features disclosed herein.

Figure 1A:
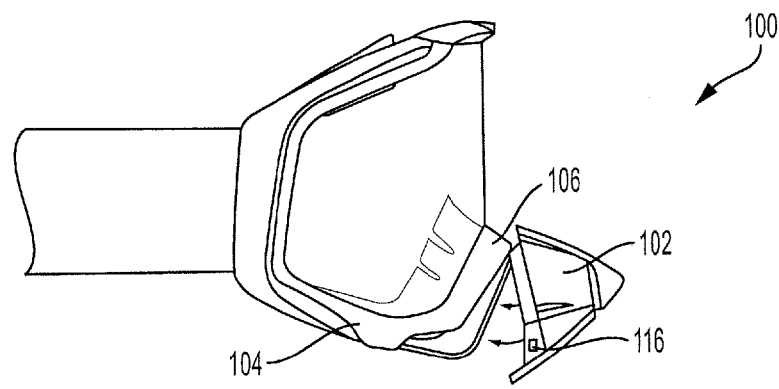
FIG. 1A is a diagram showing a side view of an exemplary embodiment of a noseguard being attached in accordance with the invention.
Figure 1B:
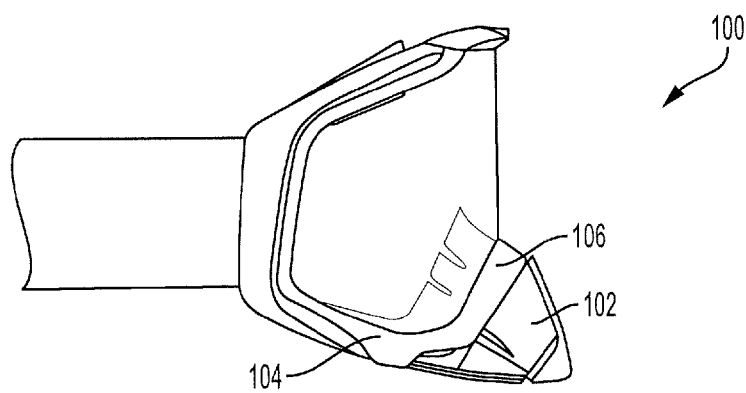
FIG. 1B is a diagram showing a side view of an exemplary embodiment of a noseguard attached in accordance with the invention.
Figure 1C:
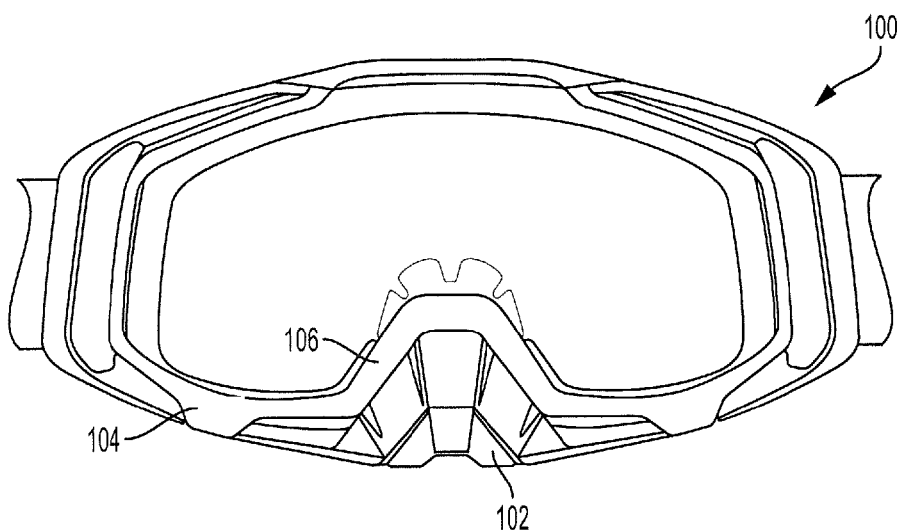
FIG. 1C is a diagram showing a front view of an exemplary embodiment of a noseguard attached in accordance with the invention.
Figure 2A:
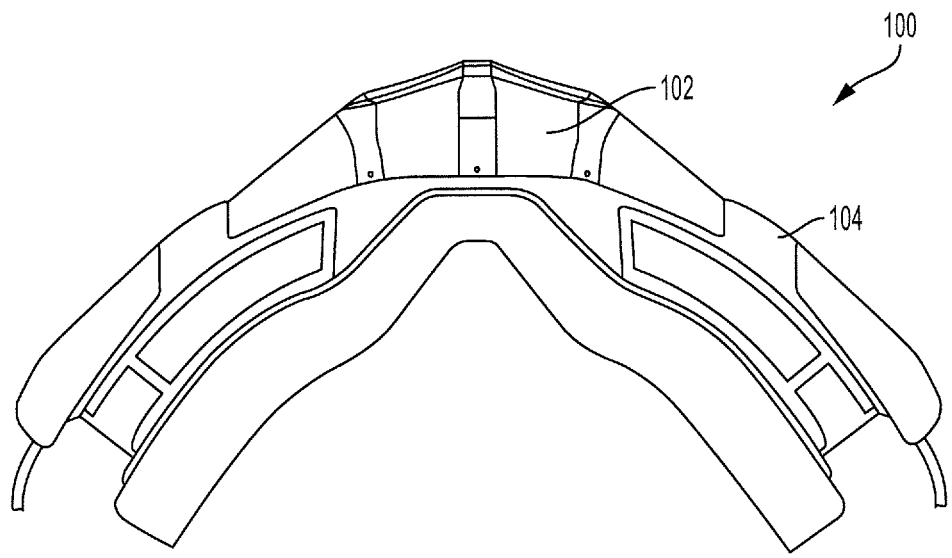
FIG. 2A is a diagram showing a bottom view of an exemplary embodiment of a noseguard attached in accordance with the invention.
Figure 2B:
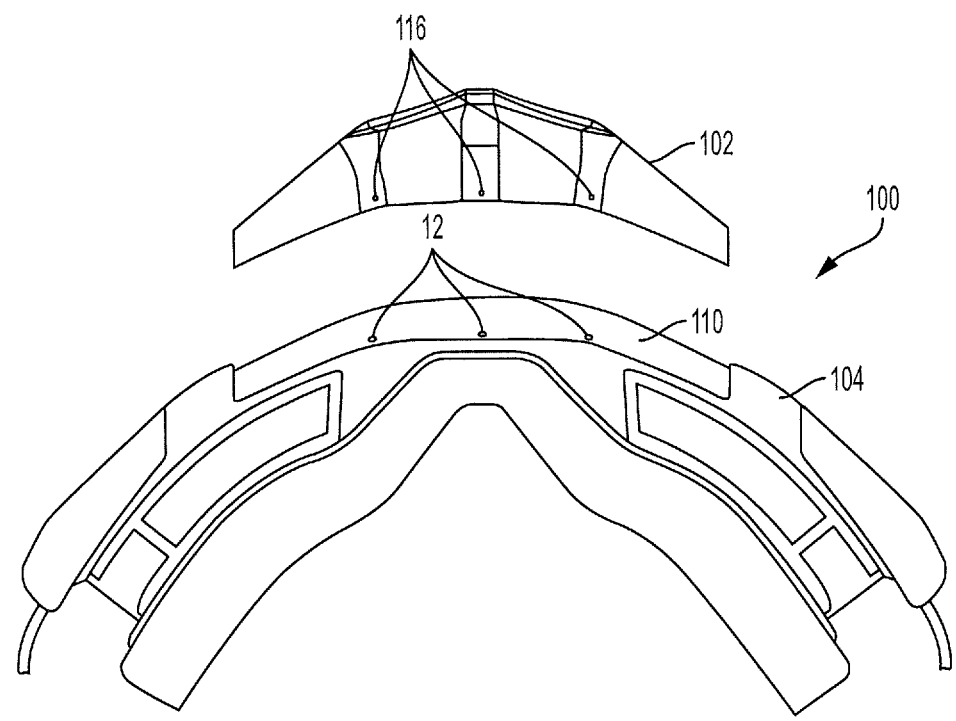
FIG. 2B is a diagram showing a bottom view of an exemplary embodiment of a noseguard removed in accordance with the invention.
Figure 3A:
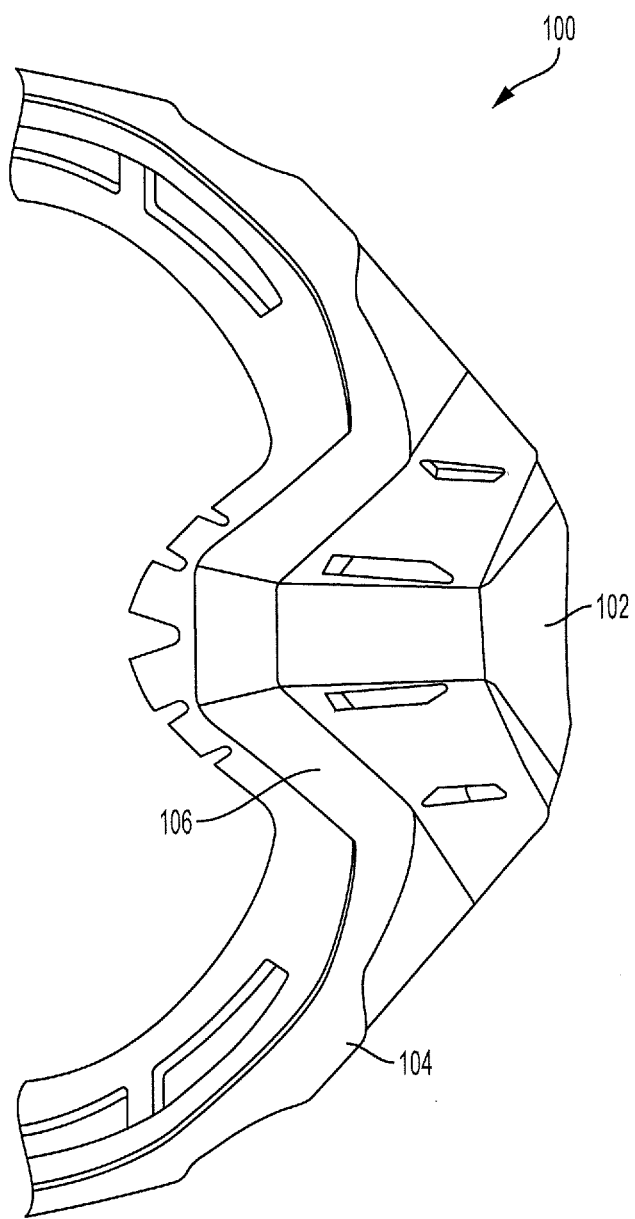
FIG. 3A is a diagram showing a front perspective view of an exemplary embodiment of a noseguard attached in accordance with the invention.
Figure 3B:
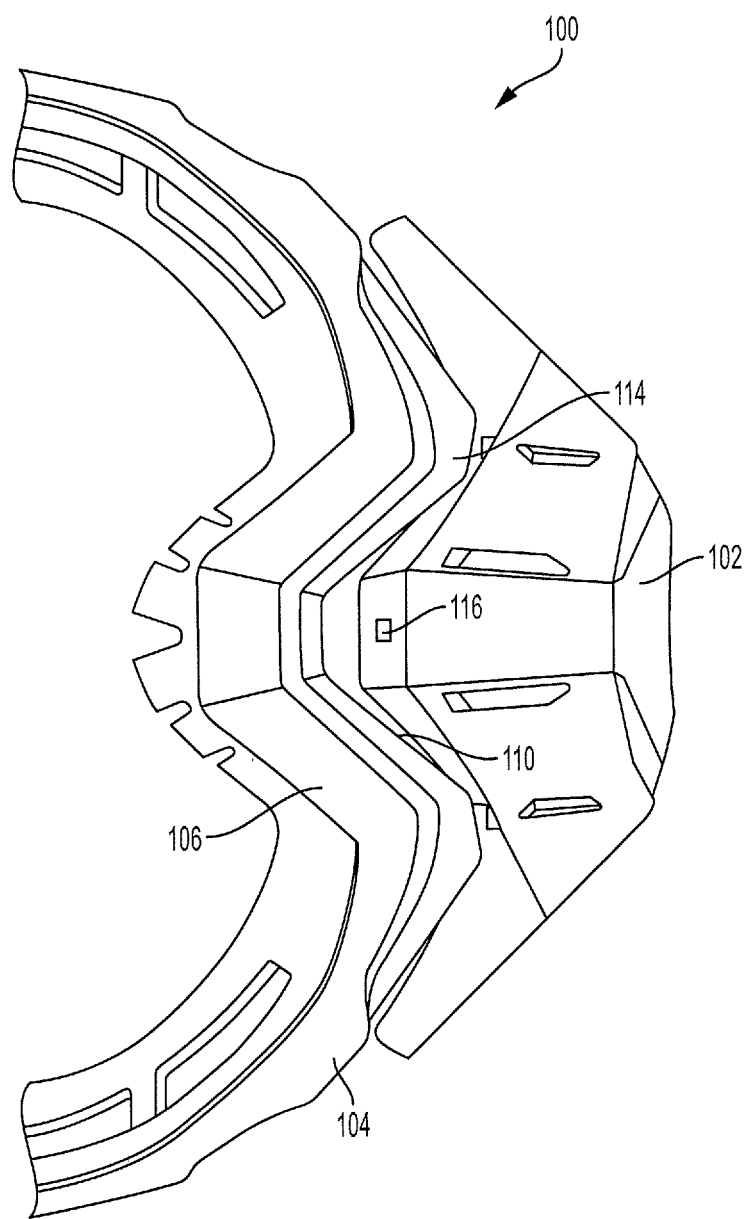
FIG. 3B is a diagram showing a front perspective view of an exemplary embodiment of a noseguard being detached in accordance with the invention.
Figure 3C:
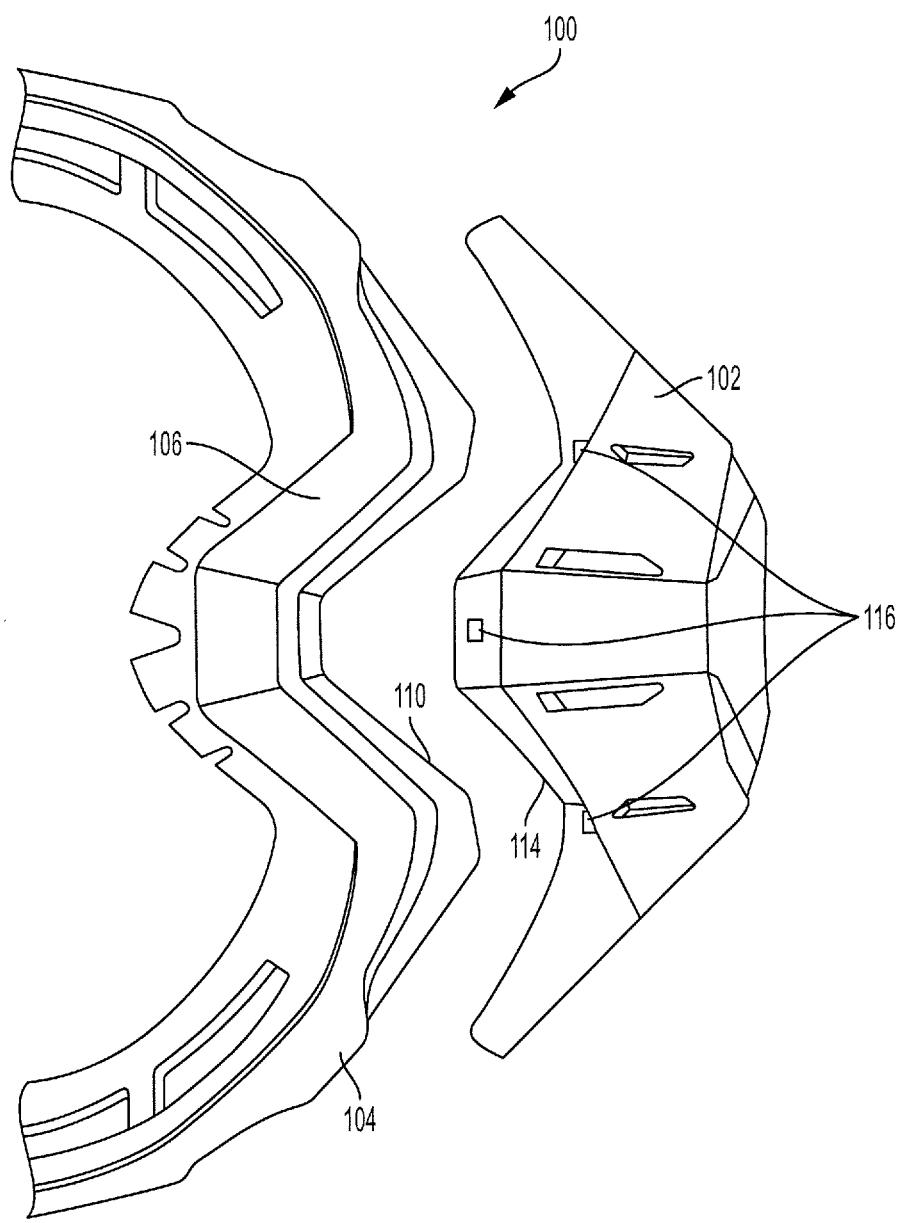
FIG. 3C is a diagram showing a front perspective view of an exemplary embodiment of a noseguard detached in accordance with the invention.
Figure 4A:
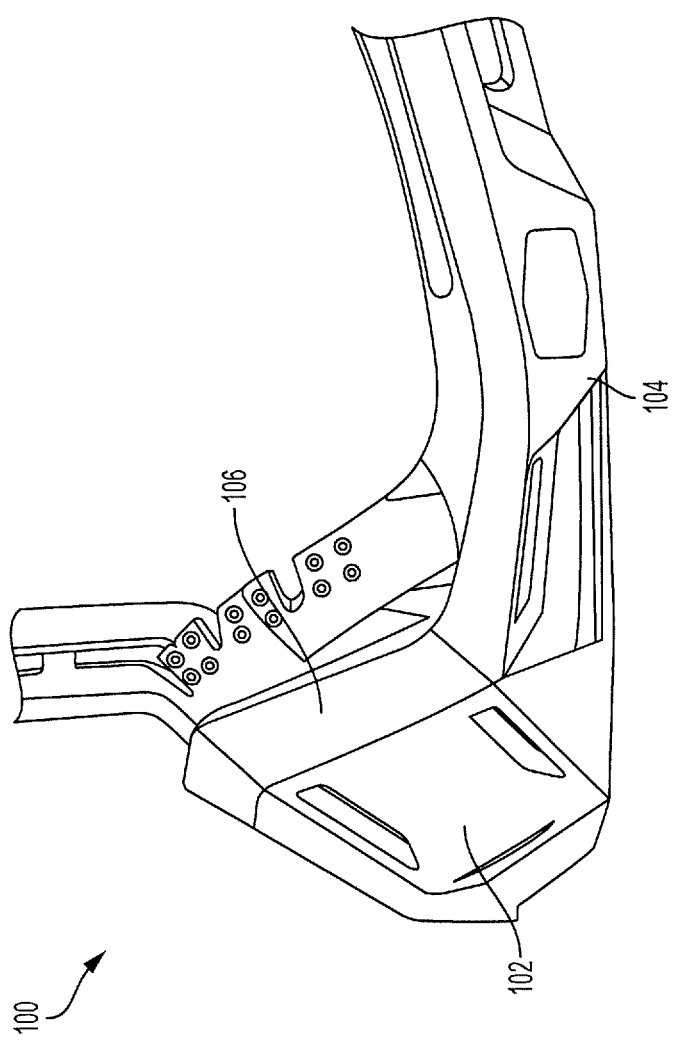
FIG. 4A is a diagram showing a side perspective view of an exemplary embodiment of a noseguard attached in accordance with the invention.
Figure 4B:
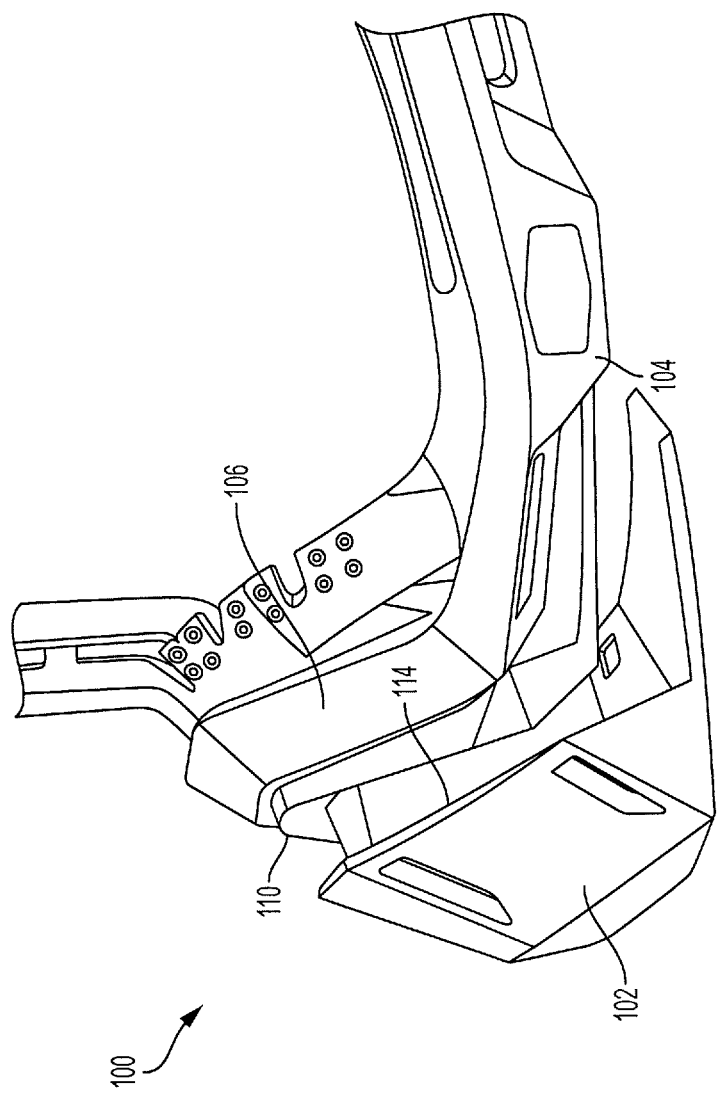
FIG. 4B is a diagram showing a side perspective view of an exemplary embodiment of a noseguard being detached in accordance with the invention.
Figure 4C:
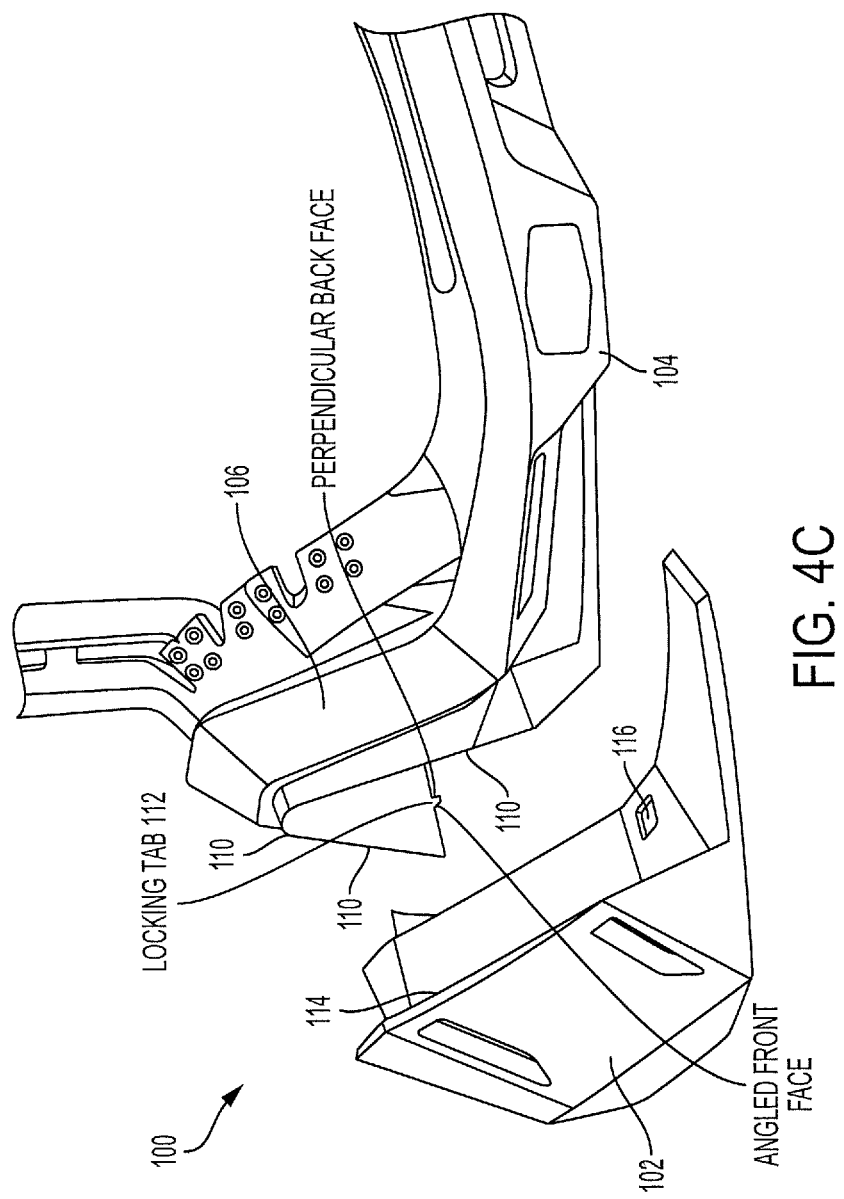
FIG. 4C is a diagram showing a side perspective view of an exemplary embodiment of a noseguard detached in accordance with the invention.
Figure 5A:
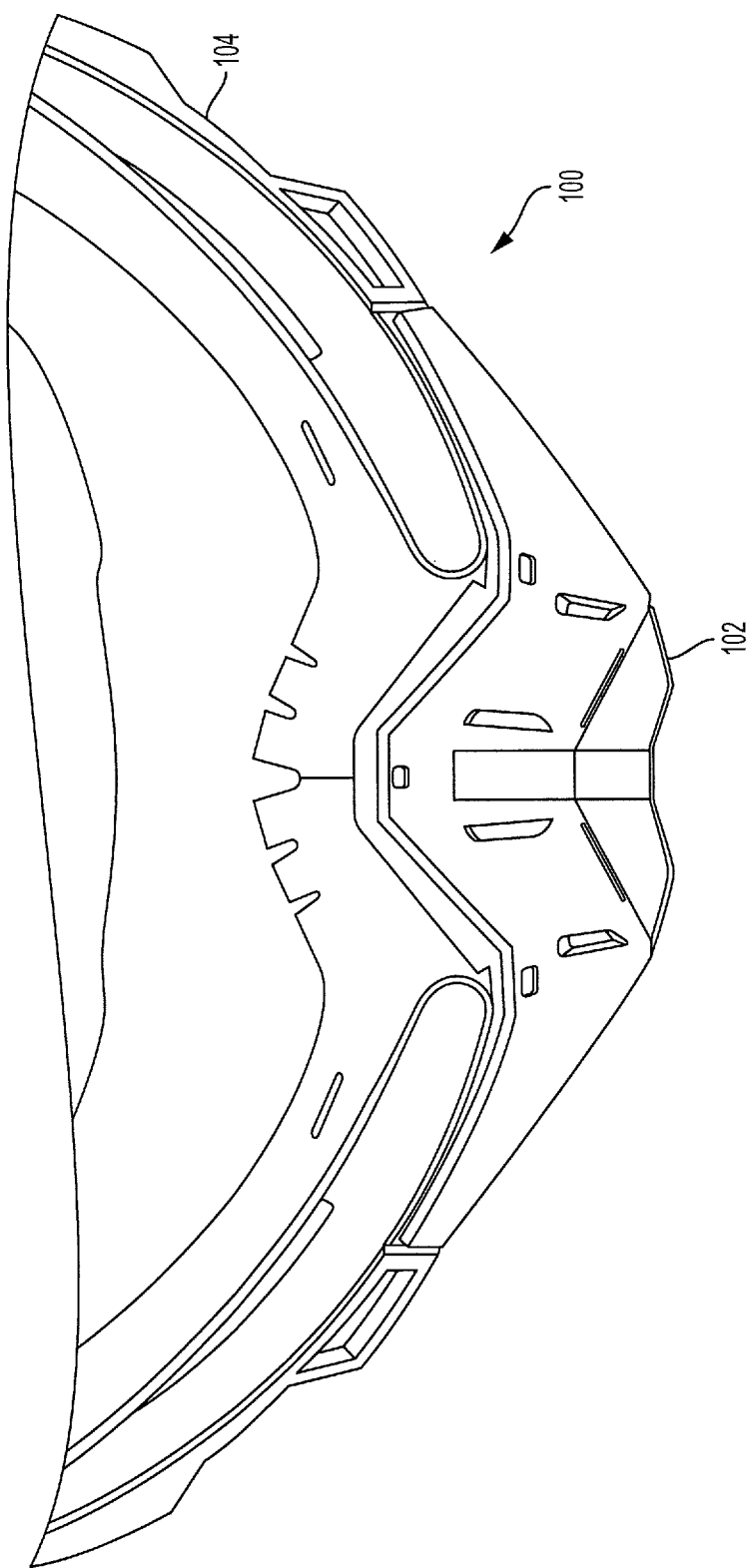
FIG. 5A is a diagram showing a bottom view of an exemplary embodiment of a noseguard attached in accordance with the invention.
Figure 5B:
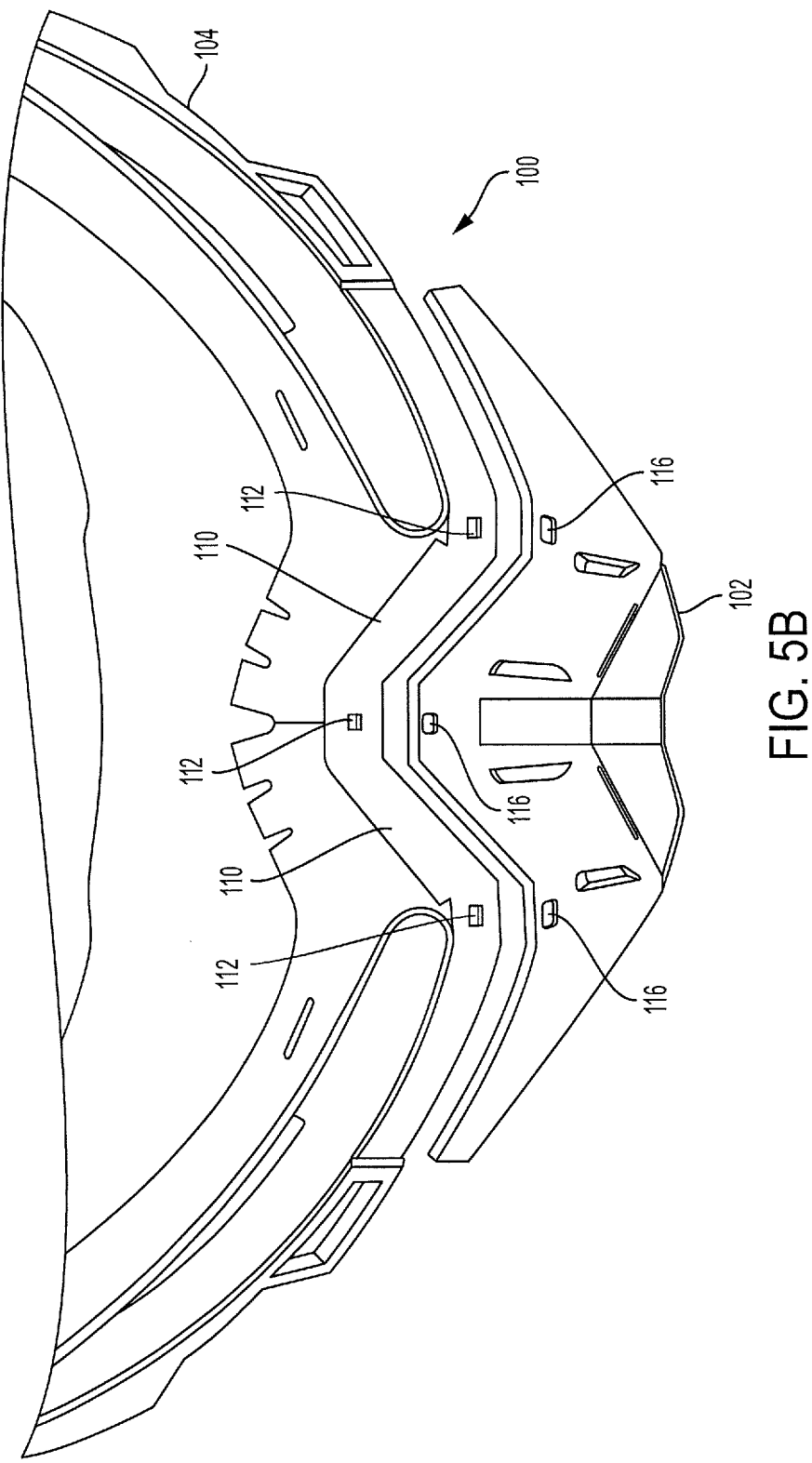
FIG. 5B is a diagram showing a bottom view of an exemplary embodiment of a noseguard detached in accordance with the invention.

Referring to FIGS. 1A through 5B, in various exemplary embodiments the present invention is a noseguard 102 that removably attaches to the frame 104 of a goggle 100. The nose region 106 of the frame 104 extends generally over the bridge of the user's nose. As illustrated in the figures, the nose region 106 of the frame of the goggle comprises a relatively thin engagement region 110 that extends from the front of frame 104. As seen in FIGS. 2B and 5B, the underside of the nose region of the goggle frame has a plurality of locking tabs 112 that extend down from a relatively planar surface of the engagement region 110 of the goggle frame 104. The locking tabs have a forward facing surface that is angled from front to back, and a back facing surface that extends generally perpendicular from the generally planar surface of the goggle frame. The locking tabs may have a generally triangular or quadrilateral cross-section.

The removable noseguard 102 has a channel 114 that is complimentary in shape to the engagement region 110 that projects forward from the nose region 106 of the front frame such that when the noseguard 102 is pressed onto the nose region 106 of the front frame this channel 114 receives the engagement region 110 to properly position the noseguard on the front of the frame 104 of the goggle. The noseguard 102 also has a plurality of notches 116 that are sized and positioned to receive the plurality of locking tabs 112 on the frame.

When the noseguard 102 is pressed onto the nose region 106 of the front frame and the channel 114 receives the engagement region 110 of the frame, the area of the noseguard around the notches 116 can slide along the angled forward facing surface of the nose region 106, flexing to accommodate the displacement caused by the locking tabs 112 until the notches 116 are positioned to receive the locking tabs 112. Once the noseguard 102 is in position and the notches 116 are positioned over the locking tabs 112, the noseguard resiliently snaps down, receiving the locking tabs on the goggle frame into the respective notches in the noseguard. The back facing surfaces of the locking tabs then prevent the noseguard from moving forward, locking the noseguard in place.

To remove the noseguard 102, the user can grasp the noseguard and pull on it to bring the notches 116 up and over the back facing surfaces of the locking tabs 112, and release the locking tabs from the notches. Because the front frame and noseguard are both somewhat flexible, the locking tabs must be sufficiently large to maintain the noseguard in position as the frame 104 and noseguard flex during use, but not so large that they make it difficult to remove the noseguard from the goggle frame.

All of the various components shown herein may be made from any suitable material, including various polymers and/or elastomeric materials. For example, the goggle frame may be made from thermoplastic polyurethane (TPU) or any other suitable material, and the noseguard may be made from acrylonitrile butadiene styrene (ABS) or any other suitable materials.

What is claimed is:

1. A goggle having a removable noseguard, the goggle comprising:
    a flexible goggle frame having a nose region configured to extend over a bridge of a user's nose;
    the goggle frame comprising an engagement region and a plurality of locking tabs, wherein the engagement region comprises a protrusion that extends from a front of the goggle frame away from the bridge of the user's nose; and
    the removable noseguard comprising a channel complimentary in shape to the protrusion and designed to receive the protrusion to position the noseguard on the goggle frame, a noseguard bottom configured to be located proximate to a bottom of the goggle frame when the channel receives the protrusion, a noseguard top configured to be located proximate to at least a portion of the nose region, and a plurality of notches sized and positioned to receive the plurality of locking tabs to firmly attach the noseguard to the goggle frame, wherein the removable noseguard is flexible and at least one of the plurality of notches and associated locking tabs are disposed at a first height from the noseguard bottom when the channel receives the protrusion, and at least another of the plurality of notches and associated locking tabs are designed to be disposed at a second height from the noseguard bottom different from the first height, and wherein the channel comprises a groove configured to receive the protrusion to position the plurality of notches to receive the plurality of locking tabs.

2. A goggle having a removable noseguard in accordance with claim 1, wherein the locking tabs have a forward facing surface that is angled from front to back, and a back facing surface that extends generally perpendicular from the generally planar surface of the goggle frame.

3. A goggle having a removable noseguard in accordance with claim 2, wherein the locking tabs have a generally triangular cross-section.

4. A goggle having a removable noseguard in accordance with claim 2, wherein the locking tabs have a generally quadrilateral cross-section.

5. A goggle having a removable noseguard in accordance with claim 2, wherein the protrusion further comprises a first protrusion portion extending from the front of the goggle frame from the nose region; and
    at least a portion of the channel is configured to receive the first protrusion portion and be disposed adjacent to the nose region.

6. A goggle having a removable noseguard in accordance with claim 1, wherein the locking tabs are configured to extend from the goggle frame towards the user's nose when worn by the user.

7. A goggle having a removable noseguard in accordance with claim 1, wherein:
    the goggle frame comprises a frame bottom edge and the goggle frame is configured to be worn by the user such that the frame bottom edge is above a user's mouth; and
    a bottom edge of the noseguard bottom is substantially level with the frame bottom edge.

8. A goggle having a removable noseguard in accordance with claim 1, further comprising a strap attached to the goggle frame.

9. A method of using the noseguard of claim 1, the method comprising:
    positioning the noseguard such that the plurality of notches are up and over a back facing surface of each of the plurality of locking tabs; and
    releasing the plurality of locking tabs from the plurality of notches.

10. The method of claim 9, further comprising:
    receiving the noseguard with the goggle frame by interfacing the protrusion and the groove of the channel;
    flexing the plurality of notches;
    positioning the noseguard such that the plurality of notches are positioned over the plurality of locking tabs; and
    receiving, with the plurality of notches, the plurality of locking tabs.

11. The method of claim 10, further comprising preventing the noseguard from moving forward, relative to the frame, with the plurality of locking tabs.

12. A goggle having a removable noseguard in accordance with claim 2, wherein the protrusion extends along and over a nose opening of the flexible goggle frame; and
    the channel is configured to receive the protrusion such that the channel is substantially disposed along and over the nose opening.

* * * * *